US008022255B2

(12) United States Patent
Cotte et al.

(10) Patent No.: US 8,022,255 B2
(45) Date of Patent: Sep. 20, 2011

(54) PROCESS FOR PREPARING KETONES FROM ALPHA-OXO CARBOXYLATES AND ARYL BROMIDES

(75) Inventors: Alain Cotte, Leverkusen (DE); Matthias Gotta, Cologne (DE); Lukas Goossen, Kaiserslautern (DE); Felix Rudolphi, Kaiserslautern (DE); Christoph Oppel, Kaiserslautern (DE); Nuria Rodriguez Garrido, Kaiserslautern (DE)

(73) Assignee: SALTIGO GmbH, Langenfeld (DE)

( * ) Notice: Subject to any disclaimer, the term of this patent is extended or adjusted under 35 U.S.C. 154(b) by 13 days.

(21) Appl. No.: 12/388,779

(22) Filed: Feb. 19, 2009

(65) Prior Publication Data
US 2009/0221832 A1      Sep. 3, 2009

(30) Foreign Application Priority Data
Feb. 28, 2008   (DE) .................. 10 2008 011 685

(51) Int. Cl.
*C07C 49/00* (2006.01)
*A01N 35/00* (2006.01)
(52) U.S. Cl. ........................ 568/332; 514/691
(58) Field of Classification Search .................. 568/332; 514/691
See application file for complete search history.

(56) References Cited

U.S. PATENT DOCUMENTS
2008/0177114 A1   7/2008  Gossen et al. ................. 568/928

OTHER PUBLICATIONS

Goossen et. al., "A new practical ketone synthesis directly from carboxylic acids: first application of coupling reagents in palladium catalysis", Chem. Commun., 2001, pp. 2084-2085.*
Casreact abstract 149:53676, "Synthesis of ketones from alpha-oxocarboxylates and aryl bromides by Cu/Pd-catalyzed decarboxylative cross-coupling", Goossen et. al., 2008.*
P. J. Masson, D. Coup, J. Millet, N. L. Brown, *J. Biol. Chem.* 1995, 270, 2662-2668.
S. Nahm, S. M. Weinreb, *Tetrahedron Lett.* 1981, 22, 3815-3818.
E. Negishi, V. Bagheri, S. Chatterjee, F. T. Luo, J. A. Miller, A. T. Stoll, *Tetrahedron Lett.* 1983, 24, 5181-5184.
P. Knochel, M. C. P. Yeh, S. C. Berk, J. Talbert, *J. Org. Chem.* 1988, 53, 2392-2394.
M. Haddach, J. R. McCarthy, *Tetrahedron Lett.* 1999, 40, 3109-3112.
L. J. Gooβen, K. Ghosh, *Chem. Comm.* 2001, 2084-2085.
E. J. Corey, D. Seebach, *Angew. Chem.* 1965, 77, 1134-1135; *Angew. Chem. Int. Ed.* 1965, 4, 1075-1077.
Y. C. Huang, K. K. Majumdar, C. H. Cheng, *J. Org. Chem.* 2002, 67, 1682-1684.
S. Ko, B. Kang, S. Chang, *Angew. Chem.* 2005, 117, 459-461; *Angew. Chem. Int. Ed.* 2005, 44, 455-457.

Goossen, L.J., et al.; "Pd-Catalyzed Synthesis of Functionalized Arylketones from Boronic Acids and Carboxylic Acids Activated in situ with Dimethyl Dicarbonate", Synlett 2002, No. 8, pp. 1237-1240, XP002527729.
Nilsson M.; "A New Biaryl Synthesis Illustrating a Connection Between the Ullmann Biaryl Synthesis and Copper-Catalysed Decarboxylation", Acta Chemica Scandinavica, Munksgaard, Copenhagen, DK, Bd. 20, No. 2, Jan. 1, 1966, pp. 423-426, XP009075993.
Takemiya, A.; Hartwig, J.F.; "Palladium-Catalyzed Synthesis of Aryl Ketons by Coupling of Aryl Bromides with an Acyl Anion Equivalent", Journal of the American Chemical Society, Bd. 128, No. 46, 2006, pp. 14800-14801, Washington, USA, XP002527730.

\* cited by examiner

*Primary Examiner* — Janet Andres
*Assistant Examiner* — Heidi Reese
(74) *Attorney, Agent, or Firm* — Michael A. Miller

(57) ABSTRACT

A process for preparing ketones of the general formula (III)

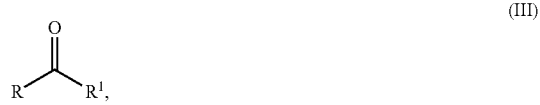

(III)

where
R is an optionally substituted carbocyclic aromatic radical having 6 to 24 carbon atoms or an optionally substituted alkyl radical or an optionally substituted heteroaromatic radical having 5 to 24 carbon atoms, and
$R^1$ is an optionally substituted carbocyclic aromatic radical having 6 to 24 carbon atoms or an optionally substituted heteroaromatic radical having 5 to 24 carbon atoms,
by reacting alpha-oxo carboxylates of the general formula (I)

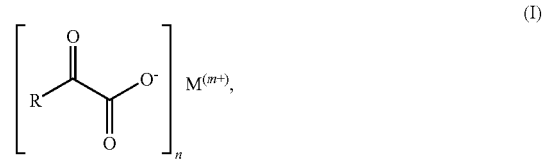

(I)

wherein
n and m is a number in the range from 1 to 6,
$M^{(m+)}$ is a cation, and
R has the meaning indicated for formula (III),
with aryl bromides of the general formula (II)

$R^1$—Br      (II)

where
$R^1$ has the meaning indicated for formula (III),
in the presence of two transition metals or compounds thereof as catalyst, is described.

9 Claims, No Drawings

PROCESS FOR PREPARING KETONES FROM ALPHA-OXO CARBOXYLATES AND ARYL BROMIDES

The present invention relates to a novel process for preparing ketones from alpha-oxo carboxylates and aryl bromides by Cu/Pd-catalysed decarboxylating cross-coupling.

Aryl ketones are important structural elements in active substances and functional materials (P. J. Masson, D. Coup, J. Millet, N. L. Brown, *J. Biol. Chem.* 1994, 270, 2662-2668). Besides classical Friedel-Crafts acylations which are carried out on an industrial scale but usually lead disadvantageously to mixtures of isomers, they are also prepared by reacting activated carboxylic acid derivatives with organometallic reagents, such as, for example, Weinreb amides with Grignard compounds (S. Nahm, S. M. Weinreb, *Tetrahedron Lett.* 1981, 22, 3815-3818). The efficiency of such cross-couplings can be increased further by using transition metal catalysts, so that even carbon nucleophiles of low reactivity are converted, for example organozinc compounds or boronic acids (E. Negishi, V. Bagheri, S. Chatterjee, F. T. Luo, J. A. Miller, A. T. Stoll, *Tetrahedron Lett.* 1983, 24, 5181-5184; P. Knochel, M. C. P. Yeh, S. C. Berk, J. Talbert, *J. Org. Chem.* 1988, 53, 2392-2394; M. Haddach, J. R. McCarthy, *Tetrahedron Lett.* 1999, 40, 3109-3112).

More convenient variants are reactions in which carboxylic acids are activated in situ, such as, for example, in palladium-catalysed direct syntheses of aryl ketones from arylboronic acids and carboxylic acids in the presence of anhydrides (L. J. Gooβen, L. Winkel, A. Döhring, K. Ghosh, J. Paetzold, *Synlett* 2002, 8, 1237-1240) or coupling reagents (L. J. Gooβen, K. Ghosh, *Chem. Comm.* 2001, 2084-2085). Although the tolerance of functional groups is distinctly improved by these methods, this procedure has serious disadvantages owing to the difficulty of obtaining boronic acids (metallation of aryl halides and subsequent reaction with trialkyl borates) or because of the disagreeable manipulation of organozinc compounds.

A converse procedure in which acylanion equivalents are coupled to carbon electrophiles is on the other hand mainly employed for synthesizing alkyl ketones (E. J. Corey, D. Seebach, *Angew. Chem.* 1965, 77, 1134-1135; *Angew. Chem. Int. Ed.* 1965, 4, 1075-1077). There are on the other hand only few examples of the catalytic arylation of acylanion equivalents, including the coupling, described by Hartwig et al., of aryl bromides with N-tert-butylhydrazones (A. Takemiya, J. F. Hartwig, *J. Am. Chem. Soc.* 2006, 128, 14800-14801). The disadvantages of all reactions of this type are the additional derivatization and hydrolysis steps, and the use of strong bases. Arylations of aldehydes with C—H activation offer an atom-economical alternative but are at present possible only with a restricted range of costly aryl iodides (Y. C. Huang, K. K. Majumdar, C. H. Cheng, *J. Org. Chem.* 2002, 67, 1682-1684; S. Ko, B. Kang, S. Chang, *Angew. Chem.* 2005, 117, 459-461; *Angew. Chem. Int. Ed.* 2005, 44, 455-457).

It has previously been demonstrated in the synthesis of biaryls from benzoic acid salts and aryl halides that decarboxylating cross-couplings may represent valuable alternatives to corresponding reactions of organometallic compounds (WO 2006/136135).

It was an object of the present invention to find a process for preparing ketones, especially aryl ketones, which start from readily available compounds and employ easily handled and low-cost catalysts.

Decarboxylation of alpha-oxo carboxylic acids of the formula (I) in the presence of a Cu catalyst in combination with a Pd-mediated cross-coupling with aryl bromides of the formula (II) results in the ketones of the formula (III):

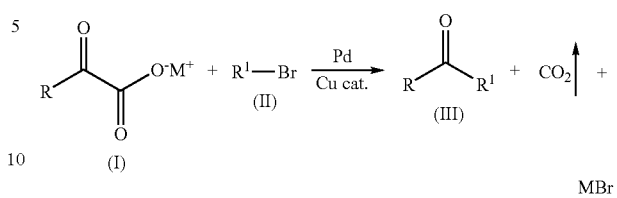

The advantage of this decarboxylating cross-coupling to prepare ketones is that, in contrast to traditional cross-coupling reactions, no organometallic reagents are necessary. Instead, easily handled, readily obtainable stable salts of alpha-oxo carboxylic acids, some of which are available industrially as intermediates in the preparation of amino acids, are used as source of acylnucleophiles.

The invention therefore relates to a process for preparing ketones of the general formula (III)

where
R is an optionally substituted carbocyclic aromatic radical having 6 to 24 carbon atoms or an optionally substituted alkyl radical or an optionally substituted heteroaromatic radical having 5 to 24 carbon atoms, and
$R^1$ is an optionally substituted carbocyclic aromatic radical having 6 to 24 carbon atoms or an optionally substituted heteroaromatic radical having 5 to 24 carbon atoms,
by reacting alpha-oxo carboxylates of the general formula (I)

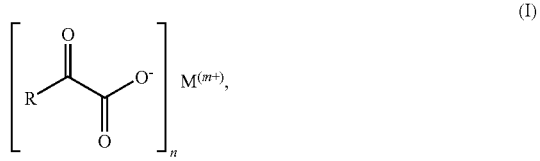

where
n and m is a number in the range from 1 to 6,
$M^{(m+)}$ is a cation, and
R has the meaning indicated for formula (III),
with aryl bromides of the general formula (II)

wherein
$R^1$ has the meaning indicated for formula (III),
in the presence of two transition metals or compounds thereof as catalyst.

The catalyst system in the process according to the invention comprises two metal components. The first component comprises a metal which can assume two oxidation states differing by one unit, particularly preferably from the series Ag(0,I), Cu (0, I, II), Mn (II, III), Fe (II, III), Co (II, III), Ni (II, III), Mo (IV, V), Ru (II, III) (suitable combinations of oxidation states by way of example in parentheses). The metal can optionally be employed in elemental form, as complex or as salt. Copper(I) compounds are particularly preferably employed, and copper(I) bromide is very particularly preferably employed as transition metal component.

The second component of the catalyst system comprises a transition metal which can assume two oxidation states differing by two units, preferably from the series Pd (0, II), Ni (0, II), Fe (−II, 0,II), Au (I, III), Rh (I, III), Pt (0, II, IV), Ru (0, II), Ir (I, III) (suitable combinations of oxidation states by way of example in parentheses). The metal can optionally be employed in elemental form, as complex or as salt. Platinum metals are particularly preferably employed, palladium compounds are very particularly preferably employed, and palladium(II) bis(1,1,1,5,5,5-hexafluoroacetylacetonate) (Pd(F$_6$-acac)$_2$) is even more preferably employed as second transition metal component.

Both metals can independently of one another optionally be stabilized by further ligands, preferably from the series amines, phosphines, N-heterocyclic carbenes, nitrites or olefins. Cyclic amines are particularly preferably used as ligands, and chelating cyclic amines from the series phenanthroline, bipyridine and terpyridine or their substituted derivatives are very particularly preferably used.

The addition of phosphine ligands has an advantageous influence on the reaction, and trialkylphosphine ligands are preferably, and tris(o-tolyl)phosphine((o-Tol)$_3$P) is particularly preferably, employed.

It is optionally possible for the actual catalysts to be generated in the reaction mixture from suitable metal precursors by adding the components (ligands) detailed above.

The catalyst system particularly preferably employed for the process according to the invention is a combination of copper(I) bromide with 1,10-phenanthroline as ligand and Pd(F$_6$acac)$_2$ with tris(o-tolyl)phosphine as ligand.

In the process according to the invention, the two catalysts are employed independently of one another in amounts of from 0.001 mol % to 100 mol % based on the carbon electrophile (R$^1$—Br), and amounts of from 0.01 mol % to 15 mol % are preferably employed.

The process according to the invention is carried out at temperatures from 20° C. to 220° C., preferably at 80° C. to 200° C. and particularly preferably at 120° C. to 180° C.

The process according to the invention is normally carried out in the presence of a solvent. Solvents which can be employed for example are one or mixtures of the starting materials, aromatic hydrocarbons (for example benzene, toluene, xylenes, ethylbenzene, mesitylene), ethers (for example 1,4-dioxane, tetrahydrofuran, methyltetrahydrofuran, dibutyl ether, methyl t-butyl ether, diisopropyl ether, diethylene glycol dimethyl ether), amides (for example dimethylformamide, diethylformamide, N-methylpyrrolidone, dimethylacetamide), aromatic amines (quinoline, pyridine), dimethyl sulphoxide, sulpholane, acetonitrile, isobutyronitrile, propionitrile, propylene carbonate and chlorinated aliphatic and aromatic hydrocarbons. Amides (for example dimethylformamide, N-methylpyrrolidone) and aromatic amines (for example quinoline, pyridine) or amide/amine mixtures are preferably employed.

The process according to the invention can preferably be carried out in such a way that traces of water can be removed by continuous azeotropic distillation during the reaction. It is also possible to operate under pressure to achieve the necessary reaction temperature.

R and R$^1$ are in the context of the invention preferably carbocyclic aromatic radicals having 6 to 24 framework carbon atoms or heteroaromatic radicals having 5 to 24 framework carbon atoms, in which zero, one, two or three carbon atoms in the framework of each ring, but at least one framework carbon atom in the complete molecule, may be replaced by heteroatoms selected from the group of nitrogen, sulphur or oxygen. The carbocyclic aromatic radicals or heteroaromatic radicals may furthermore be substituted by up to five identical or different substituents in each ring, selected from the group of hydroxy, halogen, nitro, amino, mercapto, cyano, free or protected formyl, $C_1$-$C_{12}$-alkyl, $C_1$-$C_{12}$-haloalkyl, $C_1$-$C_{12}$-alkylthio; $C_5$-$C_{14}$-aryl, $C_6$-$C_{15}$-arylalkyl, $C_1$-$C_{12}$-alkoxy and $C_1$-$C_{12}$-alkoxycarbonyl. R$^1$ is for example phenyl, tolyl, thienyl or naphthyl which is optionally substituted once, twice or three times by radicals which are each selected independently of one another from the group of $C_1$-$C_6$-alkyl, $C_1$-$C_6$-haloalkyl, $C_1$-$C_6$-alkylthio, $C_5$-$C_{14}$-aryl, $C_1$-$C_6$-alkoxy, $C_1$-$C_6$-alkoxycarbonyl, halogen, hydroxy, nitro, amino, mercapto and cyano. R$^1$ is preferably a tolyl, cyanophenyl or methoxyphenyl radical.

R is additionally in the context of the invention preferably alkyl, in each case independently is an optionally substituted straight-chain, cyclic, branched or unbranched alkyl radical. Examples of suitable substituents for the alkyl radical are $C_1$-$C_6$-alkyl, $C_1$-$C_6$-haloalkyl, $C_5$-$C_{14}$-aryl, $C_6$-$C_{15}$-arylalkyl, $C_1$-$C_6$-alkoxy, $C_1$-$C_6$-aryloxy, $C_1$-$C_6$-alkoxycarbonyl, $C_1$-$C_6$-acyloxy or halogen. Alkyl is particularly preferably for example n-propyl, isopropyl, n-butyl, tert-butyl, isobutyl, n-pentyl or cyclohexyl. R is preferably a phenyl, cyanophenyl or tert-butyl radical.

The counter-ion M$^{(m+)}$ from formula (I) is in this connection a metal cation which leads to equalization of charges, preferably from the series of metals Li, Na, K, Mg, Ca, B, Al, Ag, Cu, Mn, Fe, Co, Ni, Mo, Ru, particularly preferably from the series of sodium or potassium (n=1).

The alpha-oxo carboxylic acid salts of the formula (I) are optionally added in preformed form or are generated in situ from the alpha-oxo carboxylic acids and suitable bases.

EXAMPLES

Example 1

Preparation of tert-butyl(4-tolyl)ketone

Potassium 3,3,3-trimethylpyruvate (5.05 g, 30.0 mmol), bis(1,1,1,5,5,5-hexafluoroacetylacetonato)-palladium (104.1 mg, 0.20 mmol) and copper(I) bromide (430.4 mg, 3.00 mmol) were introduced into a reaction vessel under nitrogen, and a solution of 4-bromotoluene (3.42 g, 2.46 ml, 20 mmol), tris(o-tolyl)phosphine (182.6 mg, 0.6 mmol) and 1,10-phenanthroline (541 mg, 3.0 mmol) in 36 ml of NMP and 8.5 ml of pyridine was added. The reaction mixture was heated under reflux (170° C.) for 36 hours and, after cooling, filtered through Celite, and the filter cake was washed with diethyl ether. The resulting solution was washed three times with 1M hydrochloric acid and the aqueous phases were extracted twice with diethyl ether. The combined organic phases were washed with 100 ml of saturated sodium chloride solution, dried over magnesium sulphate and filtered. After removal of the solvent, the product was purified by Kugelrohr distillation (105° C./4×10$^{-3}$ mbar) and obtained as a yellow oil (3.17 g, 90% yield). The spectroscopy data correspond to those of tert-butyl(4-tolyl)ketone.

Example 2

Preparation of 4-methylbenzophenone

Potassium benzoylformate (225.9 mg, 1.2 mmol), bis(1,1,1,5,5,5-hexafluoroacetylacetonato)-palladium (5.2 mg, 0.01 mmol) and copper(I) bromide (21.5 mg, 0.15 mmol) were introduced into a reaction vessel under nitrogen, and a solution of 4-bromotoluene (171.0 mg, 1.0 mmol), tris(o-tolyl)phosphine (6.1 mg, 0.02 mmol) and 1,10-phenanthroline (27 mg, 0.15 mmol) in 1.5 ml of NMP and 0.5 mL of quinoline was added. The reaction mixture was heated under reflux (170° C.) for 16 hours and, after cooling, 20 ml of 1M hydrochloric acid were added, and the aqueous phases were extracted three times with ethyl acetate. The combined organic phases were concentrated and the residue was purified by chromatography. The product was obtained as a yellow oil (163 mg, 83% yield). The spectroscopic data correspond to those of 4-methylbenzophenone.

Examples 3 to 28

The following catalyst systems were found for examples 3 to 28: 15 mol % copper(I) bromide, 15 mol % 1,10-phenanthroline, 2 mol % (o-Tol)$_3$P and 1 mol % Pd(F$_6$-acac)$_2$, at 170° C. in a NMP/quinoline mixture which successfully converts a large number of aryl bromides with various alpha-oxo carboxylic acids into ketones (Table 1).

Course of the Reaction:

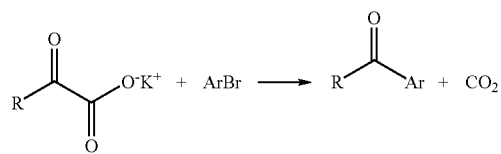

| Ex. | Product | Yield/% |
|---|---|---|
| 3 | 4-methylbenzophenone | 83 |
| 4 | 4-methoxybenzophenone | 82 |
| 5 | 4-(dimethylamino)benzophenone | 59 |
| 6 | 9-phenanthrenyl phenyl ketone | 83 |
| 7 | 4-cyanobenzophenone | 99 |
| 8 | ethyl 4-benzoylbenzoate | 70 |
| 9 | phenyl 3-pyridyl ketone | 57 |
| 10 | 2-methoxybenzophenone | 73 |
| 11 | 4,4'-dimethylbenzophenone | 72 |
| 12 | 4-methoxy-4'-methylbenzophenone | 64 |
| 13 | 4-cyano-4'-methylbenzophenone | 96 |

-continued

| Ex. | Product | Yield/% |
|---|---|---|
| 14 | (2-thienyl)-C(O)-(4-methylphenyl) | 45 |
| 15 | (2,4-dimethylphenyl)-C(O)-(4-methylphenyl) | 52 |
| 16 | (tert-butyl)-C(O)-(4-methylphenyl) | 90 |
| 17 | phenyl-C(O)-(4-SMe-phenyl) | 67 |
| 18 | phenyl-C(O)-(4-Cl-phenyl) | 56 |
| 19 | phenyl-C(O)-(1-naphthyl) | 82 |
| 20 | phenyl-C(O)-(4-C(O)Me-phenyl) | 78 |
| 21 | phenyl-C(O)-(4-CF$_3$-phenyl) | 72 |
| 22 | phenyl-C(O)-(3-thienyl) | 50 |
| 23 | phenyl-C(O)-(2,6-dimethylphenyl) | 26 |
| 24 | isobutyl-C(O)-(4-methylphenyl) | 69 |
| 25 | (4-Me$_2$N-phenyl)-C(O)-(4-methylphenyl) | 59 |
| 26 | (2-furyl)-C(O)-(4-methylphenyl) | 51 |
| 27 | benzyl-C(O)-(4-methylphenyl) | 34 |
| 28 | (2,4,6-trimethylphenyl)-C(O)-(4-methylphenyl) | 5 |

The substituent from the alpha-oxo carboxylic acid is drawn to the left of the carbonyl group in Table 1.

It can be inferred from Table 1 that the alpha-oxo carboxylic acids react both with electron-rich and electron-poor aryl and heteroaryl bromides to give the phenyl ketones in good yields, with many functional groups being tolerated, inter alia esters, ketones and nitriles. On the other hand, 4-bromotoluene could be coupled in good yields with various alkyl-, aryl- and heteroaryl-substituted alpha-oxo carboxylic acids, and therefore the broadly applicable novel synthesis method for preparing aryl ketones was demonstrated.

The invention claimed is:

1. Process for preparing ketones of the general formula (III)

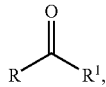

where
R is an optionally substituted carbocyclic aromatic radical having 6 to 24 carbon atoms or an optionally substituted alkyl radical or an optionally substituted heteroaromatic radical having 5 to 24 carbon atoms, and
$R^1$ is an optionally substituted carbocyclic aromatic radical having 6 to 24 carbon atoms or an optionally substituted heteroaromatic radical having 5 to 24 carbon atoms,
by reacting alpha-oxo carboxylates of the general formula (I)

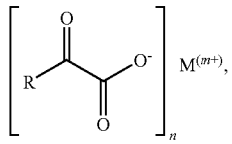

wherein
n and m is a number in the range from 1 to 6,
$M^{(m+)}$ is a cation, and
R has the meaning indicated for formula (III),
with aryl bromides of the general formula (II)

where
$R^1$ has the meaning indicated for formula (III),
in the presence of a catalyst system comprising two components wherein each component comprises, independently of one another, at least one metal or metal compound.

2. Process according to claim 1, wherein each component of the catalyst system comprise different transition metals and/or transition metal compounds, wherein one transition metal or one transition metal compound is selected from those able to assume oxidation states differing from one another by one unit, and the other transition metal or the other transition metal compound is selected from those able to assume oxidation states differing from one another by two units.

3. Process according to claim 1, wherein one component of the catalyst system comprise one transition metal or the transition metal compound selected from the series of metals consisting of Ag, Cu, Mn, Fe, Co, Ni, Mo, and Ru and the other catalyst component comprises transition metal or transition metal compound selected from the series of metals consisting of Pd, Ni, Fe, Au, Rh, Pt, Ru, and Ir.

4. Process according to claim 1, wherein at least one of the metals in either the first component or the second component is stabilized by ligands from the series of amines, N-heterocyclic carbenes, nitriles, olefins or phosphines.

5. Process according to claim 4, wherein the ligand is a chelating amine from the series phenanthroline, bipyridine, terpyridine and/or a trialkylphosphine.

6. Process according to claim 1, wherein a combination of copper(I) bromide with 1,10-phenanthroline as ligand and bis(1,1,1,5,5,5-hexafluoroacetylacetonato)palladium with tris(o-tolyl)phosphine as ligand is employed as the catalyst system.

7. Process according to claim 1, wherein the amounts of the two components of the catalyst system are employed independently of one another in an amount from 0.001 mol % to 100 mol % based on the compound of the formula (II).

8. Process according to claim 1, wherein the radical R in compound of the formula (III) is a phenyl, cyanophenyl or tert-butyl radical.

9. Process according to claim 1, wherein the radical $R^1$ in the compound of the formula (III) is a tolyl, cyanophenyl or methoxyphenyl radical.

* * * * *